(12) United States Patent
Svensson et al.

(10) Patent No.: US 8,761,883 B2
(45) Date of Patent: Jun. 24, 2014

(54) PHYSIOLOGICALLY ADAPTED CARDIAC RESYNCHRONIZATION THERAPY

(75) Inventors: Tomas Svensson, Stockholm (SE); Andreas Blomqvist, Taby (SE); Andreas Karlsson, Solna (SE); Michael Broome, Ekero (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/578,553

(22) PCT Filed: Aug. 31, 2011

(86) PCT No.: PCT/EP2011/064965
§ 371 (c)(1),
(2), (4) Date: Aug. 10, 2012

(87) PCT Pub. No.: WO2013/029669
PCT Pub. Date: Mar. 7, 2013

(65) Prior Publication Data
US 2013/0053917 A1    Feb. 28, 2013

(51) Int. Cl.
*A61N 1/37*    (2006.01)
(52) U.S. Cl.
USPC .......................................... 607/28; 607/119
(58) Field of Classification Search
USPC ................ 607/9, 17, 24–28, 115–122
See application file for complete search history.

(56) References Cited

U.S. PATENT DOCUMENTS

| | | | |
|---|---|---|---|
| 7,840,266 B2 | 11/2010 | Libbus et al. | |
| 7,881,810 B1 | 2/2011 | Chitre et al. | |
| 2003/0204232 A1 | 10/2003 | Sommer et al. | |
| 2004/0015193 A1 | 1/2004 | Lamson et al. | |
| 2006/0149184 A1 | 7/2006 | Soykan et al. | |
| 2010/0268059 A1 | 10/2010 | Ryu et al. | |
| 2010/0280565 A1 | 11/2010 | Santamore et al. | |

FOREIGN PATENT DOCUMENTS

| | | | |
|---|---|---|---|
| WO | 2004050180 A2 | 6/2004 | |
| WO | 2004050180 A3 | 11/2004 | |

OTHER PUBLICATIONS

Intern'l Search Report—PCT/EP2011/064965, filed Aug. 31, 2011.
Written Opinion—PCT/EP2011/064965, filed Aug. 31, 2011.

*Primary Examiner* — Rex R Holmes

(57) ABSTRACT

An implantable medical device is connectable to an epicardial left ventricular lead having at least one epicardial electrode and a myocardium penetrating catheter with at least one endocardial electrode and present in a lumen of the lead. The device comprises a pulse generator controller that controls a ventricular pulse generator to generate pulses to be applied to the epicardial and endocardial electrodes. The controller uses an endocardial-to-epicardial time interval or epicardial-to-endocardial time interval to coordinate endocardial and epicardial activation of the left ventricle to thereby achieve cardiac pacing that closely mimics the natural electrical activation pattern of a healthy heart.

15 Claims, 6 Drawing Sheets

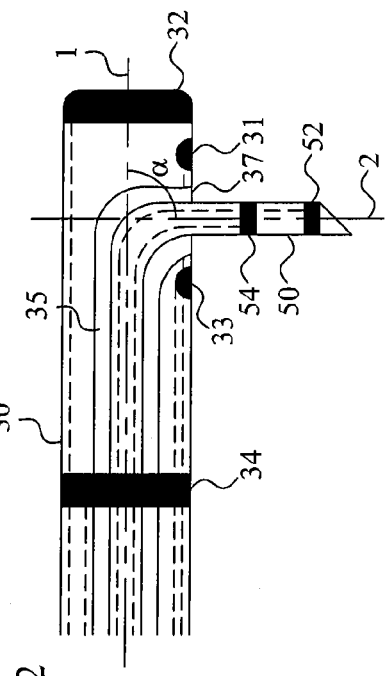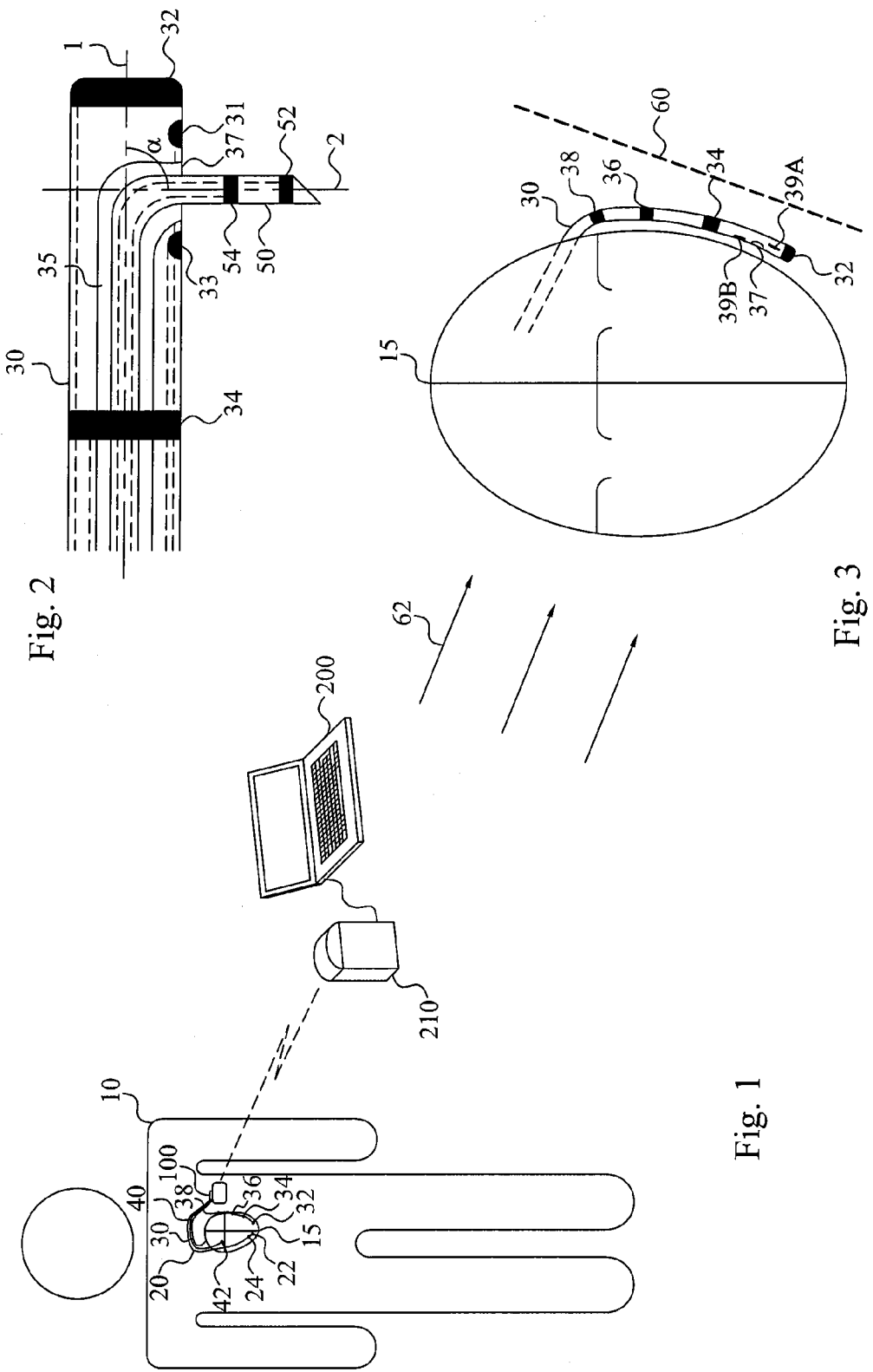

PHYSIOLOGICALLY ADAPTED CARDIAC RESYNCHRONIZATION THERAPY

TECHNICAL FIELD

The embodiments generally relate to cardiac resynchronization therapy (CRT), and in particular to such CRT that mimics the normal physiology of the heart.

BACKGROUND

In patients in need of cardiac resynchronization therapy (CRT) the left ventricle electrodes are almost exclusively placed epicardially, either directly on the epicardial surface or through a coronary vein. This results in a pacing activation sequence very different from normal physiology, where the myocardium normally is activated from the endocardial surface to the epicardium resulting in specific improvement of cardiac efficiency and reduction of shear forces within the ventricular wall. The natural activation sequence is generally better than "total synchronization" in terms of achieving physiologically suitable heart contraction and should be mimicked as close as possible.

Somewhat diverging views exist about how the myocardium is organized. The cardiac surgeon Gerald D Buckberg at UCLA bases his understanding of cardiac action on the Spanish anatomist Francis Torrent-Guasp who claims that the left ventricular myocardium can be dissected and functionally described as consisting of a myocardial band divided in three "sub-bands": the basal loop, the descending loop and the ascending loop. These loops are activated in sequence resulting in an initial basal contraction rotating the basal heart clock-wise as seen from apex and reducing the diameter of the mitral annulus, an early systolic apical clockwise torsion movement followed by a counterclockwise torsion during the main part of systolic emptying. Of specific interest is the initiation of diastole, where Buckberg and others think that an active untwisting movement (caused by muscular contraction in epicardial layers of the "ascending loop") adds to the elastic recoil reinforcing left ventricular filling.

Other researchers claim that the myocardial band does not exist as an anatomical entity and that the myocardium is better described as a continuous syncytium of muscular cells with varying orientations depending on the distance from the endocardium.

Although different views exist it is still accepted that an initial basal contraction decreases mitral annular diameter early in systole. The majority of the left ventricular mass is activated from the endocardium to the epicardium resulting in an initial clock-wise rotation and somewhat later a dominating systolic counter clock-wise rotation associated with left ventricular shortening. An "untwist" is seen during diastole accompanied by lengthening and widening of the left ventricle.

There is, thus, a need for a technique that can be used to provide CRT that is physiologically adapted to subjects in need thereof.

U.S. Pat. No. 7,840,266 discloses a lead assembly adapted for placement in a coronary sinus and having a left ventricular electrode adapted to deliver CRT to reduce ventricular wall stress. A fat pad electrode is also provided on the lead assembly to be positioned proximal to a parasympathetic ganglia located in a fat pad bounded by the inferior vena cava and the left atrium. The fat pad electrode is adapted to stimulate the parasympathetic ganglia to reduce ventricular wall stress.

US 2004/0015193 relates to implanting pacing electrodes. A guided tissue penetrating catheter is inserted into a blood vessel and a penetrator is advanced from the catheter to a target location. A pacing electrode may be delivered through a lumen in the penetrator.

U.S. Pat. No. 7,881,810 discloses how a heart chamber may be accessed via the pericardial space of the heart. The pericardial space is accessed via a transmyocardial approach or a subxiphoid approach. A lead may, thus, be routed into the pericardial space, through myocardial tissue and into the heart chamber.

US2010/0280565 relates to a catheter-based system for implantation of pacing leads or intramural myocardial reinforcement devices within the myocardial wall of the heart to provide improved cardiac function.

SUMMARY

It is a general objective to provide CRT that is physiologically adapted.

It is a particular objective to provide CRT that coordinates left ventricular endocardial and epicardial depolarization.

These and other objectives are met by embodiments disclosed herein.

Briefly, an aspect of the embodiments defines an implantable medical device (IMD) comprising a lead connector that is connectable to an epicardial left ventricular (LV) lead. The epicardial LV lead comprises at least one epicardial electrode provided in connection with its distal end. The epicardial LV lead also has a lumen housing a myocardium penetrating catheter with at least one endocardial electrode. The lead connector then has connector terminals that are connectable to respective electrode terminals at the proximal end of the epicardial LV lead to thereby achieve an electrical connection between the IMD and the epicardial and endocardial electrodes. A ventricular pulse generator is arranged in the IMD connected to the lead connector and configured to generate pacing pulses to be applied to the endocardial and epicardial electrodes. A pulse generator controller is connected to and controls the operation of the ventricular pulse generator. The pulse generator controller in particular controls the ventricular pulse generator to apply a pacing pulse at an epicardial (or endocardial) electrode of the epicardial LV lead following expiry of an intrinsic endocardial-to-epicardial (or epicardial-to-endocardial) time interval if no depolarization is detected at the epicardial (or endocardial) electrode from the start of and up to the end of the intrinsic endocardial-to-epicardial (or epicardial-to-endocardial) time interval for a cardiac cycle. The intrinsic endocardial-to-epicardial (or epicardial-to-endocardial) time interval is then started from detection of a depolarization at an endocardial (or epicardial) electrode of the epicardial LV lead.

The pulse generator controller is, alternatively or in addition, configured to control the ventricular pulse generator to apply a pacing pulse to the epicardial (or endocardial) electrode of the epicardial LV lead following expiry of a paced endocardial-to-epicardial (or epicardial-to-endocardial) time interval if no depolarization is detected at the epicardial (or endocardial) electrode from the start of and up to the end of the paced endocardial-to-epicardial (or epicardial-to-endocardial) time interval for a cardiac cycle. The paced endocardial-to-epicardial (or epicardial-to-endocardial) time interval is then started from application of a pacing pulse by the ventricular pulse generator at an endocardial (or epicardial) electrode of the epicardial LV lead.

Another aspect of the embodiments relates to a cardiac resynchronization therapy method. The method involves detecting a depolarization at an endocardial (or epicardial) electrode of the epicardial LV lead. This depolarization detection starts an intrinsic endocardial-to-epicardial (or epicardial-to-endocardial) time interval. During the intrinsic endocardial-to-epicardial (or epicardial-to-endocardial) time interval the method monitors for a depolarization at an epicardial (or endocardial) electrode of the epicardial LV lead. If no such depolarization is detected during the intrinsic endocardial-to-epicardial (or epicardial-to-endocardial) time interval a pacing pulse is applied to the epicardial (or endocardial) electrode at the end of the intrinsic endocardial-to-epicardial (or epicardial-to-endocardial) time interval.

A further aspect of the embodiments relates to a cardiac resynchronization method. The method involves applying a pacing pulse at an endocardial (or epicardial) electrode of the epicardial LV lead. This pacing pulse application triggers the start of a paced endocardial-to-epicardial (or epicardial-to-endocardial) time interval. During the paced endocardial-to-epicardial (or epicardial-to-endocardial) time interval the method monitors for any depolarization at an epicardial (or endocardial) electrode of the epicardial LV lead. If no such depolarization is detected following expiry of the paced endocardial-to-epicardial (or epicardial-to-endocardial) time interval a pacing pulse is applied to the epicardial (or endocardial) electrode at the end of the paced endocardial-to-epicardial (or epicardial-to-endocardial) time interval.

The aspects of the embodiments provide a coordination of endocardial and epicardial depolarization and activation at the left ventricle of a subject's heart. This coordinated endocardial and epicardial depolarization closely mimics the natural activation sequence of a healthy heart and thereby promotes efficient contraction of the heart and the left ventricle during systole.

BRIEF DESCRIPTION OF THE DRAWINGS

The invention, together with further objects and advantages thereof, may best be understood by making reference to the following description taken together with the accompanying drawings, in which:

FIG. 1 is a schematic overview of a human subject equipped with an implantable medical device according to an embodiment;

FIG. 2 is schematic, partially cross-sectional, view of a distal portion of an epicardial left ventricular lead according to an embodiment;

FIG. 3 schematically illustrates a technique of correctly positioning an epicardial left ventricular lead according to an embodiment;

DETAILED DESCRIPTION

Figure 8:
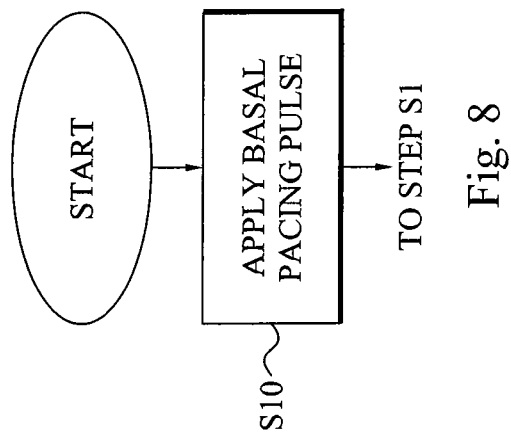
FIG. 8 is a flow diagram illustrating an additional step according to an embodiment of the cardiac resynchronization therapy method.

Throughout the drawings, the same reference numbers are used for similar or corresponding elements.

The embodiments generally relate to cardiac resynchronization therapy (CRT), and in particular to such CRT that mimics the normal physiology of the heart. In more detail, the present embodiments enable CRT that is capable of combined and coordinated endocardial and epicardial pacing at the left ventricle of a heart in a patient.

The present embodiments employ a special epicardial left ventricular (LV) lead or pacing catheter that comprises both one or more epicardial electrodes and one or more endocardial electrodes. Hence, the embodiments introduce a further aspect and dimension to traditional CRT by not only being able to define and employ atrioventricular (AV) delays or intervals and/or interventricular (W) delays or intervals for coordinating cardiac pacing but adds the possibility of employing endocardial-to-epicardial and/or epicardial-to-endocardial delays or intervals for coordinating cardiac pacing.

The possibility of pacing both endocardially and epicardially at the left ventricle implies that the pacing sequence will more closely mimic the natural depolarization propagation of a healthy heart. It is believed that the pacing achievable according to the embodiments will improve the contraction pattern of the heart during systole and in particular promote the left ventricular rotation and thereby left ventricular contraction.

The epicardial LV lead of the embodiments is a so-called coronary sinus lead or transvenous LV lead having the possibility of achieving both epicardial and endocardial pacing as disclosed herein.

FIG. 1 is a schematic overview of a subject, represented by a human subject 10 having an implantable medical device (IMD) 100 according to the embodiment. The IMD 100 is implanted in the subject 10 in order to provide pacing therapy to the subject's heart 15. The IMD 100 can be in the form of a pacemaker or an implantable cardioverter-defibrillator (ICD). The IMD 100 is, during operation in the subject's body, connected to an epicardial LV lead 30 having at least one epicardial electrode 32, 34, 36, 38 and at least one endocardial electrode (shown in FIGS. 2 and 5). As is well known in the art, an epicardial LV electrode 30 is provided on the outside of the heart 15 typically in the coronary venous system, e.g. in a left lateral vein or a postero-lateral vein. The epicardial LV lead 30 enables the IMD 100 to apply pacing pulses to the left ventricle and sense electrical activity from the left ventricle. The IMD 100 can also be connected to other cardiac leads, for instance a right ventricular (RV) lead 20 and/or an atrial lead 40. An RV lead 20 is typically provided inside the right ventricle of the heart 15 and comprises one or more electrodes 22, 24 that can be used by the IMD 100 to apply pacing pulses to the right ventricle and/or sense electrical activity from the right ventricle. An atrial lead 40, typically a right atrial (RA) lead 40 having at least one electrode 42 arranged in or in connection with the right atrium, can be used by the IMD 100 in order to provide atrial pacing and/or sensing. Instead of or as a complement to an RA lead, the IMD 100 can be connected to a left atrial (LA) lead.

FIG. 1 additionally illustrates a non-implantable data processing device 200, such as in the form of a programmer, a home monitoring device or a physician's workstation. The data processing device 200 comprises or is connected to a communication module or device 210 that is capable of wirelessly communicating with the IMD 100, preferably through radio frequency (RF) based communication or inductive telemetry. The data processing device 200 can then use the communication module 210 in order to interrogate the IMD 100 for diagnostic data recorded by the IMD 100 employing the electrodes 22, 24, 32, 34, 36, 38, 42 of the connected cardiac lead(s) 20, 30, 40. Furthermore, the data processing device 200 can be used to program the IMD 100, such as by setting one or more programmable CRT parameters. According to the present embodiments, the data processing device 200 can in particular be used in order to define so called time intervals, such as paced and/or intrinsic or sensed time intervals or delays, employed by the IMD 100 to coordinate pacing at multiple cardiac sites. In particular paced and/or intrinsic endocardial-to-epicardial and/or epicardial-to-endocardial time intervals that are used by the IMD 100 according to the embodiments can be programmed into the IMD 100 by the data processing device 200. If the IMD 100 is also connected to an RV lead 20 and/or an RA lead 40 as shown in FIG. 1, the data processing device 200 can program paced and/or intrinsic interventricular (VV) time intervals and/or atrioventricular (AV) time intervals into the IMD 100.

The communication module 210 and the data processing device 200 can be separate devices as illustrated in FIG. 1, either wired connected or using a wireless connection, such as Bluetooth®, an infrared (IR) connection or an RF connection. In an alternative embodiment, the functionality and equipment of the communication module 210 can be housed within the data processing device 200.

The IMD of the present embodiments is connectable to an epicardial LV lead that comprises both epicardial and endocardial electrodes. This epicardial LV lead has a myocardium penetrating part that enters the myocardium after a transvenous lead approach to thereby position the endocardial electrode(s) in subendocardial tissue of the left ventricle. This way of accessing the endocardium is much safer in terms of the risk of thrombosis as compared to using a left ventricular lead that is present inside the left ventricle. In addition, a single epicardial LV lead of the embodiments can be used to both achieve endocardial and epicardial left ventricular pacing and sensing, whereas if a lead present inside the left ventricle would have been used that lead would then have to be complemented with a separate epicardial lead in order to achieve both endocardial and epicardial left ventricular pacing and sensing.

With reference to FIG. 2, the epicardial LV lead 30 comprises at least one epicardial electrode 32, 34 provided in connection with a distal end of the epicardial LV lead 30. The at least one epicardial electrode 32, 34 is connected to a respective electrode terminal provided in connection with the opposite proximal end of the epicardial LV lead 30. This proximal end is designed to be connected to the IMD, which is further described herein. The electrical connection between the epicardial electrode(s) 32, 34 and the electrode terminal(s) is achieved by a respective electrical conductor running along the body of the lead. These electrical conductors are indicated as broken lines in FIG. 2.

The epicardial LV lead 30 also comprises a lumen 35 that houses a myocardium penetrating catheter 50 that is movable within the lumen 35 and relative the epicardial LV lead 30. The myocardium penetrating catheter 50 comprises at least one endocardial electrode 52, 54. The at least one endocardial electrode 52, 54 is electrically connected, through a respective electrical conductor, to a respective electrode terminal provided in connection with the proximal end of the epicardial LV lead 30. The endocardial electrode 52, 54 of the myocardium penetrating catheter 50 is configured to be positioned in the myocardium, i.e. in a sub-endocardial site, and is thereby interposed between the endocardium and the epicardium.

The myocardium penetrating catheter 50 is designed to be moved inside the lumen 35 and extend beyond the outer surface (lateral/envelope surface) of the epicardial LV lead 30. The distal end of the myocardium penetrating catheter 50 is sharpened or needle-like in order to be able to penetrate through the myocardium to thereby move the distal end of the myocardium penetrating catheter 50 and thereby the at least one endocardial electrode 52, 54 to a sub-endocardial site and thereby reach endocardial fibers. However, the myocardium penetrating catheter 50 is preferably not moved that far so that it penetrates into the left ventricular cavity. There is a clear sensation to the physician when the myocardium penetrating catheter 50 has pierced through the myocardium and reaches the endocardial fibers. That tissue provides more resistance than the intramural myocardium and the sensation is sufficient to not advance the myocardium penetrating catheter 50 too far to risk penetration into the left ventricular cavity.

The lumen 35 of the epicardial LV lead 30 is preferably turned at its distal end so that the myocardium penetrating catheter 50 can protrude out from the epicardial LV lead 30 on its lateral or envelope surface as indicated in FIG. 2. The turn of the lumen 35 could be close to 90° as shown in FIG. 2, which causes the myocardium penetrating catheter 50 to protrude at least close to perpendicular to the main axis 1 of the epicardial LV lead 30. The embodiments are, however, not limited thereto. In clear contrast, the turn of the lumen 35 can be designed in any other angle larger than 0° and smaller than 180°. It is generally preferred if the angle $\alpha$ between the main axis 2 of the protruding part of the myocardium penetrating catheter 50 and the main axis 1 of the epicardial LV lead 30 is in the interval $0°<\alpha\leq90°$, preferably $40\leq°\alpha\leq60°$, such as about 50°.

The lumen 35 can end in an opening 37 in the lateral surface of the epicardial LV lead 30. The myocardium penetrating catheter 50 is then moved partly out from the lumen 35 through the opening 37. In an alternative approach the lumen 35 does not have any opening but instead ends at the outer insulating tubing of the epicardial LV lead 30 or is provided with a dedicated cover. The lumen 35 is then initially closed. However, as the myocardium penetrating catheter 50 is moved through the lumen 35, for instance by pushing at the proximal end of the myocardium penetrating catheter 50, the myocardium penetrating catheter 50 will penetrate through the outer insulating tubing or the cover to thereby protrude and extend beyond the lateral surface of the epicardial LV lead 30.

When implanting the epicardial LV lead 30 of the embodiments, the epicardial LV lead 30, with the myocardium penetrating catheter 50 present inside the lumen 35 of the epicardial LV lead 30 is inserted in the coronary vein system of the subject's heart as a traditional LV lead. Once the intended lead position has been reached in the coronary vein system the epicardial LV lead 30 is oriented so that the myocardium penetrating catheter 30, when moved out of the opening 37 and passing the lateral surface of the epicardial LV lead 30, faces and will penetrate the myocardium. This orientation of the epicardial LV lead 30 can be performed according to various embodiments as disclosed here below.

In an embodiment impedance measurements are employed to aid when rotating the epicardial LV lead 30 around its central axis 1 to face the lumen opening 37 in the correct direction towards the myocardium. Such impedance measurements can be used since the pericardial fluid surrounding the coronary vein on all sides but the side facing the myocardium has different electrical properties as compared to the myocardium. Table 1 below lists resisitivity values for different tissue types.

TABLE 1

Resistivity for different tissue types

| Tissue type | Resistivity ρ [Ωm] |
|---|---|
| Blood (hematocrit = 45) | 1.6 |
| Plasma | 0.7 |
| Heart muscle (longitudinal) | 2.5 |
| Heart muscle (transverse) | 5.6 |

Thus, myocardium (heart muscle) will have a different resistivity, typically higher resistivity, as compared to the pericardial fluid, which has a resistivity close to plasma.

Impedance measurements can be conducted by two electrodes 31, 33 arranged close to the opening 37 in the lumen 35, for instance on either side of the opening 37 or the part of the lateral surface at which the myocardium penetrating catheter 50 exits the lumen 35, see FIG. 2. The electrodes 31, 33 are connected to a respective electrical conductor indicated by broken lines in FIG. 2. In such a case, an electric pulse or pulse train having a known current can be applied over the two electrodes 31, 33 while the voltage of the resulting electric signal is measured over the electrodes 31, 33 to thereby enable calculation of a bipolar impedance based on the known current and the measured voltage.

These impedance measurements are performed while rotating the epicardial LV lead 30. The correct orientation of the epicardial LV lead 30 is reached when the impedance is at its highest value with the opening 37 and the myocardium penetrating catheter 50 facing the myocardium.

In an alternative embodiment, the epicardial LV lead 30 only has one electrode 31 for the impedance measurements and then uses the most distal endocardial electrode 52 of the myocardium penetrating catheter 50 as the other electrode. In this approach the myocardium penetrating catheter 50 is pushed slightly out of the lumen 35 during the measurements.

Figure 4A:
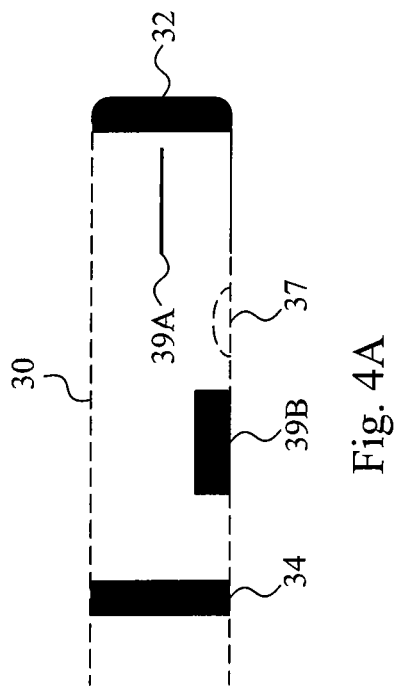
FIGS. 4A and 4B are different views of a distal portion of an epicardial left ventricular lead according to an embodiment.
Figure 4B:
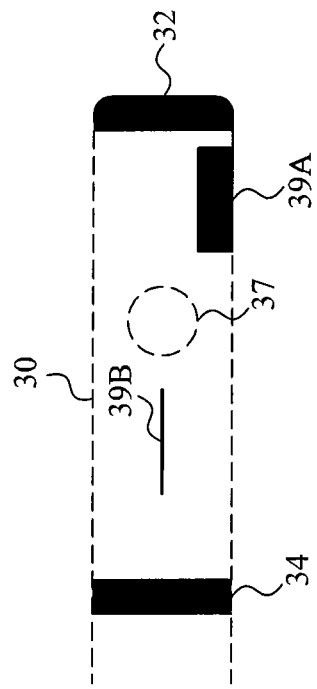

Another approach is to use fluoroscopy to the guide the orientation of the epicardial LV lead 30 instead of impedance measurements. FIG. 3 illustrates this approach. The epicardial LV lead 30 is in this embodiment equipped with at least two markers 39A, 39B that can be seen on an X-ray image taken by an X-ray detector 60 when applying X-rays 62. The X-rays 62 should preferably be set up in such a way that they are perpendicular to the main axis of the epicardial LV lead 30 and perpendicular to the preferred movement direction for the myocardium penetrating catheter, see FIG. 3. FIGS. 4A and 4B schematically illustrate two X-ray images taken with the setup as illustrated in FIG. 3 and rotated 90° relative each other. It is seen from FIGS. 4A and 4B that the markers 39A, 39B can be used to determine how the epicardial LV lead 30 is oriented and what direction the opening 37 is facing.

Further approaches for orienting the epicardial LV lead that can be used according to the embodiments are disclosed in US 2004/0015193 and include imageable markings, sensors, imaging transducers, electro-anatomical mapping and catheter guidance systems. For further examples of lead orientation, reference is made to U.S. Pat. Nos. 5,830,222; 6,068, 638; 6,071,292; WO 99/49793; WO 99/49910 and WO 02/062265, the disclosure of these documents with regard to lead orientation and verification being expressly incorporated herein by reference.

Figure 6:
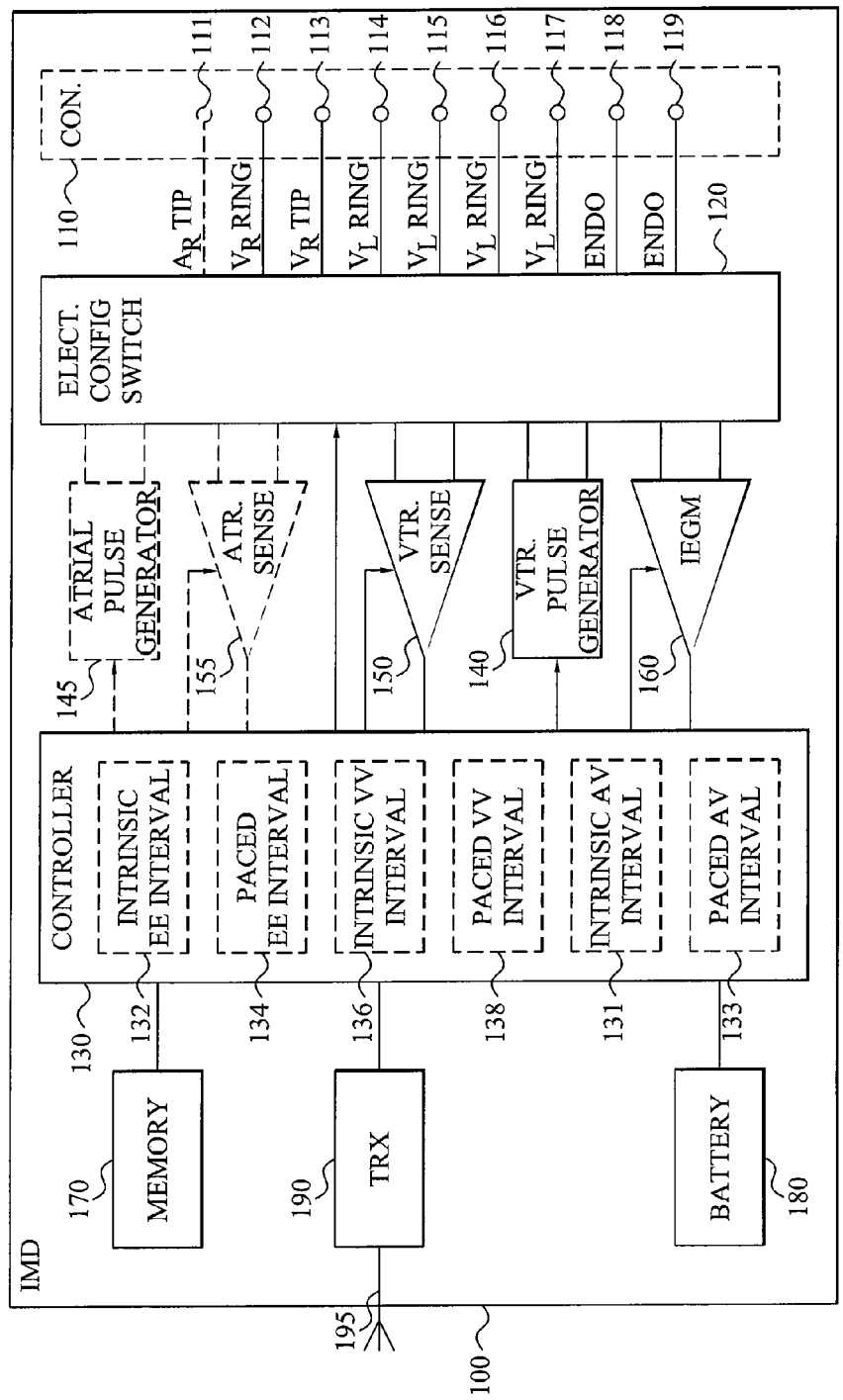
FIG. 6 is a schematic block diagram of an implantable medical device (IMD) according to an embodiment.

FIG. 6 is a schematic block diagram of an embodiment of an IMD 100 according to the embodiments. The IMD 100 comprises a lead connector 110 having connector terminals 111-119 configured to be connected to matching electrode terminals of one or more cardiac leads. In particular, the lead connector 110 is connectable to an epicardial LV lead 30 as previously described herein. Thus, the lead connector 110 comprises multiple connector terminals 114-119, each of which is electrically connectable to a respective electrode terminal of the epicardial LV lead 30. In FIG. 6, the epicardial LV lead 30 as illustrated in FIGS. 1-3 have been assumed, i.e. an epicardial LV lead 30 having four epicardial electrodes 32, 34, 36, 38, and two endocardial electrodes 52, 54 on the myocardium penetrating catheter 50. The lead connector 110 therefore comprises four connector terminals 114-117 for electrical connection with the epicardial electrodes 32, 34, 36, 38 and two connector terminals 118, 119 for electrical connection with the endocardial electrodes 52, 54. It is anticipated by the embodiments that with other embodiments of the epicardial LV lead having different number of epicardial electrodes and/or different number of endocardial electrodes the number of connector terminals in the lead connector 110 is correspondingly changed. According to the embodiments, the epicardial LV lead comprises at least one epicardial electrode and at least one endocardial electrode in order to be able to provide both endocardial and epicardial LV pacing and sensing.

The IMD 100 also comprises a ventricular pulse generator 140 connected to the lead connector 110, optionally through an electronic configuration switch 120. The ventricular pulse generator 140 is configured to generate pacing pulses to be applied, through the optional switch 120 and the lead connector 110, to the at least one epicardial electrode and the at least one endocardial electrode of the epicardial LV lead.

The ventricular pulse generator 140 is connected to and controlled by a pulse generator controller, represented by a general controller 130 in FIG. 6. The controller 130 controls the particular pacing pattern to be applied to the left ventricle of the subject's heart by the epicardial LV lead and the ventricular pulse generator 140. In particular, the controller 130 has access to and uses time intervals or delays to determine whether and when pacing pulses should be applied to an endocardial LV site and/or an epicardial LV site. Such a time interval defines the length of a time period during which the IMD 100 senses for any spontaneous depolarization at a particular site in the heart. This time interval runs from a time point of electrical activity at another site in the heart. Thus, from this time point of electrical activity at one cardiac site the controller 130 starts a timer while the IMD 100 senses for any electrical activity, i.e. spontaneous depolarization at a target cardiac site. Once a defined time interval has passed as determined from the timer and no electrical activity has been sensed at the target cardiac site, the controller 130 triggers the ventricular pulse generator 140 to generate and apply, through the switch 120 and the lead connector 110, a pacing pulse to the electrode of the epicardial LV lead positioned at or close to the target cardiac site.

The controller 130 can then have access to so-called intrinsic time intervals or delays and/or paced time intervals or delays. The former, i.e. intrinsic time interval, is employed if the electrical activity, which triggered the start of the timer, was a spontaneous depolarization at the cardiac site sensed by the IMD 100. In clear contrast, paced time interval is employed if the electrical activity instead was due to application of a pacing pulse by the IMD 100 at the cardiac site.

The present embodiments can be used in connection with having both an intrinsic time interval and a paced time interval. Information of these time intervals is then preferably stored in the memory 170 connected to and accessible to the controller 130. In an alternative approach, the IMD 100 uses the same length of the time interval irrespective of whether it is due to intrinsic electric activity or paced electric activity. In such a case, a single time interval can be used irrespective of whether the start of the time interval is due to a sensed depolarization or due to application of a pacing pulse. Further embodiments include using only intrinsic time interval(s) or only having paced time interval(s).

According to the embodiments, the time intervals employed by the controller 130 is endocardial-to-epicardial and/or epicardial-to-endocardial time intervals. Thus, the IMD 100 is thereby capable of applying pacing pulses to both at least one endocardial site of the left ventricle and to at least one epicardial site of the left ventricle using the epicardial LV lead of the embodiments.

In a general embodiment, the controller 130 controls the ventricular pulse generator 140 to apply a pacing pulse to one of an epicardial electrode of the epicardial LV lead and an endocardial electrode of (the myocardium penetrating catheter of) the epicardial LV lead following expiry of an intrinsic time interval from detection, by a ventricular sensing circuit or detector 150, of a depolarization at the other of an epicardial electrode and an endocardial electrode of the epicardial LV lead if no depolarization is detected at the one of an epicardial electrode and an endocardial electrode following detection of the depolarization by the ventricular sensing circuit 150 for a cardiac cycle. Thus, the controller 130 triggers the ventricular pulse generator 140 to generate a pacing pulse to be applied to an epicardial (or endocardial) electrode following expiry of the intrinsic time interval if no depolarization is detected at the epicardial (or endocardial) electrode prior to expiry of the intrinsic time interval. In this case, the intrinsic time interval is started with the detection or sensing of a depolarization at an endocardial (or epicardial) electrode of the epicardial LV lead.

In addition, or alternatively, the controller 130 is configured to control the ventricular pulse generator 140 to apply a pacing pulse to the one of an epicardial electrode and an endocardial electrode following expiry of a paced time interval from application of a pacing pulse at the other of an epicardial electrode and an endocardial electrode if no depolarization is detected at the one of an epicardial electrode and an endocardial electrode following application of the pacing pulse at the other of an epicardial electrode and an endocardial electrode but prior to expiry of the paced time interval for a cardiac cycle. Thus, the controller 130 triggers the ventricular pulse generator 140 to generate a pacing pulse to be applied to an epicardial (or endocardial) electrode following expiry of the paced time interval if no depolarization is detected at the epicardial (or endocardial) electrode prior to expiry of the paced time interval. In this case, the paced time interval is started with the generation and/or application of a pacing pulse at an endocardial (or epicardial) electrode of the epicardial LV lead.

In a first approach, the intrinsic and/or paced time intervals are intrinsic and/or paced endocardial-to-epicardial time intervals. In an embodiment of this first approach, the controller 130 is configured to control the ventricular pulse generator 140 to apply a pacing pulse to an epicardial electrode of the epicardial LV lead following expiry of an intrinsic endocardial-to-epicardial time interval. This intrinsic endocardial-to-epicardial time interval starts at the detection of an endocardial depolarization at an endocardial electrode of the epicardial LV lead using the ventricular sensing circuit 150. The pacing pulse is applied to the epicardial electrode if no epicardial depolarization is detected at the epicardial electrode following detection of the endocardial depolarization but prior to expiry of the intrinsic endocardial-to-epicardial time interval for a cardiac cycle.

This embodiment therefore enables epicardial depolarization no later than at the end of the intrinsic endocardial-to-epicardial time interval from when a spontaneous depolarization is detected at the endocardial electrode. Thus, if the depolarization wave has, at the end of the intrinsic endocardial-to-epicardial time interval, not reached the epicardial site at which the epicardial electrode is positioned, an epicardial depolarization is triggered by application of a pacing pulse to the epicardial electrode.

In another embodiment of the first approach, the controller 130 is configured to control the ventricular pulse generator 140 to apply a pacing pulse to an epicardial electrode of the epicardial LV lead following expiry of a paced endocardial-to-epicardial time interval. This paced endocardial-to-epicardial time interval is started at the application of a pacing pulse from the ventricular pulse generator 140 at an endocardial electrode of the myocardium penetrating catheter of the epicardial LV lead. The pacing pulse is applied to the epicardial electrode if no epicardial depolarization is detected at the epicardial electrode following the application of the endocardial pacing pulse but prior to expiry of the paced endocardial-to-epicardial time interval for a cardiac cycle.

In similarity to the embodiment described above, this embodiment provides epicardial depolarization no later than at the end of the paced endocardial-to-epicardial time interval from application of a pacing pulse at an endocardial site of the left ventricle. Thus, if the depolarization wave has, at the end of the paced endocardial-to-epicardial time interval, not reached the epicardial site an epicardial depolarization is triggered by application of a pacing pulse at the epicardial electrode.

The IMD 100 can be configured to operate according to one of these two embodiments or could be configured to use both intrinsic and paced endocardial-to-epicardial time intervals. In the latter case, the intrinsic and paced time intervals can have the same length or have different lengths.

FIG. 6 schematically illustrates the controller 130 as having access to the intrinsic endocardial-to-epicardial time interval 132 and the paced endocardial-to-epicardial time interval 134.

In this first approach the IMD 100 thereby enables a pacing pattern that mimics the natural pacing pattern of a healthy heart, i.e. LV depolarization first occurs at the endocardium and then travels through the myocardium to the epicardial part of the left ventricle. This pacing pattern will thereby enhance the contraction of the left ventricle and contribute to counter clock-wise rotation associated with left ventricular shortening.

For some subjects it might be more beneficial to use an opposite pacing pattern, i.e. first depolarization at the epicardium followed by endocardial depolarization. This is in particular advantageous for patients having inferred depolarization propagation causing a significant delay in epicardial activation. This is generally referred to as "line of block" in the art.

In such a case, the controller 130 controls the ventricular pulse generator to apply a pacing pulse to an endocardial electrode of the epicardial LV lead following expiry of an intrinsic epicardial-to-endocardial time interval from detection of an epicardial depolarization at an epicardial electrode of the epicardial LV lead. The pacing pulse is applied if no endocardial depolarization is detected at the endocardial electrode from the start of and up to the end of the intrinsic epicardial-to-endocardial time interval. In addition, or alternatively, controller 130 controls the ventricular pulse generator 140 to apply a pacing pulse to an endocardial electrode following expiry of a paced epicardial-to-endocardial time interval from application of a pacing pulse at an epicardial electrode. The pacing pulse is applied at the endocardial electrode if no endocardial depolarization is detected at the endocardial electrode from the start of and up to the end of the paced epicardial-to-endocardial time interval.

The IMD 100 can be configured to only employ endocardial-to-epicardial pacing patterns or only employ epicardial-to-endocardial pacing patterns. A further alternative is to have an IMD 100 capable of using both type of pacing patterns and select between them based on the current conditions of the subject.

The endocardial and epicardial pacing with the epicardial LV lead can further be complemented with an initial basal pacing. Such initial basal contraction is believed to promote reduction of the mitral annular diameter early in systole. The epicardial LV lead 30 then comprises a basal epicardial electrode 38, see FIGS. 1 and 3, which is provided on the epicardial LV lead 30 to be positioned at or adjacent to a basal portion of the left ventricle of the heart 15. In such a case, the controller 130 is configured to control the ventricular pulse generator 140 to apply a pacing pulse at the basal epicardial electrode prior to detection of the epicardial/endocardial depolarization or prior to the application of the pacing pulse at the epicardial/endocardial electrode. Thus, basal left ventricular pacing precedes the previously described epicardial and endocardial pacing/depolarization. This means that the reduction in mitral annular diameter will occur prior to the rotation and shortening of the left ventricle and therefore closely mimics the mechanical contraction pattern of a healthy heart.

The IMD 100 and the lead connector 110 are advantageously connected to a right ventricular lead in addition to the epicardial LV lead. The lead connector 110 then comprises connector terminals 112, 113 to match and be electrically connected to the electrodes of the right ventricular lead. In FIG. 6, a bipolar right ventricular lead 20 as illustrated in FIG. 1 has been assumed with a tip electrode 22 and a ring electrode 24. If other right ventricular lead configurations are employed the connector terminals of the lead connector 110 are correspondingly updated. According to the embodiments, the right ventricular lead comprises at least one electrode provided in connection with its distal end.

In this approach, the coordination of endocardial-epicardial LV pacing is complemented with coordinated interventricular pacing. A first embodiment uses a controller 130 that is configured to control the ventricular pulse generator 140 to apply a pacing pulse at an endocardial (or epicardial) electrode of the epicardial LV lead following expiry of an intrinsic ventricular-to-ventricular (VV) time interval from detection of a depolarization at a right ventricular (RV) electrode. This pacing pulse is applied to the endocardial (or epicardial) electrode if no depolarization is detected at the endocardial (or epicardial) electrode from the start of and up to the end of the intrinsic VV time interval for the cardiac cycle.

In a second embodiment the controller 130 is configured to control the ventricular pulse generator 140 to apply a pacing pulse at an endocardial (or epicardial) electrode of the epicardial LV lead following expiry of a paced VV time interval from application of a pacing pulse at an RV electrode. This endocardial (or epicardial) pacing pulse is applied if no depolarization is detected at the endocardial (or epicardial) electrode from the start of and up to the end of the paced VV time interval for the cardiac cycle.

In these embodiments the IMD 100 and the controller 130 therefore have access to two different types of time intervals that control the pacing pattern. First right ventricular depolarization occurs, either spontaneously or by the generation, by the ventricular pulse generator 140, of a pacing pulse that is applied to an electrode of the right ventricular lead. Following this right ventricular depolarization an intrinsic/paced VV time interval is started while the ventricular sensing circuit 150 monitors for any endocardial (or epicardial) depolarization in the left ventricle. If no such depolarization is detected following expiry of the intrinsic/paced VV time interval, an endocardial (or epicardial) pacing pulse is generated by the ventricular pulse generator 140 and applied to the endocardial (or epicardial) electrode of the epicardial LV lead. This in turn triggers the start of the paced endocardial-to-epicardial (or epicardial-to-endocardial) time interval described in the foregoing. If endocardial (or epicardial) depolarization is detected by the ventricular sensing circuit 150 before the expiry of the paced/intrinsic VV time interval, the detection of this endocardial (or epicardial) depolarization triggers the start of the intrinsic endocardial-to-epicardial (or epicardial-to-endocardial) time interval.

Thus, in these embodiments the depolarization pattern will generally be right ventricular depolarization, followed by endocardial left ventricular depolarization and followed by epicardial left ventricular depolarization or right ventricular depolarization, followed by epicardial left ventricular depolarization and followed by endocardial left ventricular depolarization. If basal LV pacing is also used as disclosed in the foregoing, this basal LV pacing preferably precedes the right ventricular depolarization.

In an alternative approach, the intrinsic/paced VV time interval is started from a LV electrical activity, which implies that LV depolarization precedes RV depolarization.

The controller 130 then controls the ventricular pulse generator 140 to apply a pacing pulse at a right ventricular electrode following expiry of an intrinsic VV time interval from detection of a depolarization at an endocardial (or epicardial) electrode of the epicardial LV lead if no depolarization is detected at the right ventricular electrode from the start of and up to the end of the intrinsic VV time interval.

Alternatively, or in addition, the controller 130 is configured to control the ventricular pulse generator 140 to apply a pacing pulse at the right ventricular electrode following expiry of a paced VV time interval from application of a pacing pulse to an endocardial (or epicardial) electrode of the epicardial LV lead if no depolarization is detected at the right ventricular electrode from the start of and up to the end of the paced VV time interval.

In this embodiment, detection of depolarization by the ventricular sensing circuit 150 at an endocardial (or epicardial) electrode of the epicardial LV lead triggers both the intrinsic VV time interval and the intrinsic endocardial-to-epicardial (or epicardial-to-endocardial) time interval. Correspondingly, application of a pacing pulse by the ventricular pulse generator 140 at an endocardial (or epicardial) electrode of the epicardial LV lead triggers both the paced VV time interval and the paced endocardial-to-epicardial (or epicardial-to-endocardial) time interval. The particular depolarization pattern achieved for a cardiac cycle with these time intervals depends on the length of the intrinsic/paced VV interval as compared to the length of the intrinsic/paced endocardial-to-epicardial (or epicardial-to-endocardial) time interval. If the intrinsic/paced VV time interval is shorter, the depolarization sequence will generally be endocardial LV depolarization, followed by RV depolarization and followed by epicardial LV depolarization or epicardial LV depolarization, followed by RV depolarization and followed by endocardial LV depolarization. If instead the intrinsic/paced VV time interval is longer the depolarization sequence will generally be endocardial LV depolarization, followed by epicardial LV depolarization and followed by RV depolarization or epicardial LV depolarization, followed by endocardial LV depolarization and followed by RV depolarization.

Generally subjects suffering from right bundle branch block (RBBB) would benefit from pacing at the right ventricle prior to left ventricular pacing according to the embodiments. However, also other subjects meeting the demands for CRT could benefit from preexcitation in the right ventricle, i.e. RV activation prior to LV activation.

These embodiments can be complemented with basal LV pacing as previously discussed. In such a case, this basal LV pacing preferably precedes the endocardial (or epicardial) LV depolarization.

A further variant is to trigger the intrinsic/paced endocardial-to-epicardial (or epicardial-to-endocardial) time interval from spontaneous/paced endocardial (or epicardial) LV depolarization and then apply epicardial (or endocardial) pacing if no spontaneous depolarization is detected at the epicardial (or endocardial) electrode of the epicardial LV lead. Such spontaneous depolarization then triggers the intrinsic VV time interval and the paced VV time interval is started at the application of the epicardial (or endocardial) pacing pulse. In this approach, LV endocardial and epicardial depolarization will typically precede the RV depolarization.

In these embodiments, the controller 130 preferably has access to the intrinsic endocardial-to-epicardial and/or epicardial-to-endocardial time interval 132, the paced endocardial-to-epicardial and/or epicardial-to-endocardial time interval 134, the intrinsic VV time interval 136 and the paced VV time interval 138. These time intervals can then be stored in the memory 170 as previously discussed.

The above described embodiments thereby complement the traditional CRT approach using intrinsic/paced VV time intervals with intrinsic/paced endocardial-to-epicardial and/or epicardial-to-endocardial time intervals.

The particular time intervals employed by the controller 130 of the IMD 100 can be set by the subject's physician and are then programmed into the IMD 100. The IMD 100 preferably comprises a transceiver (TRX) 190, or separate transmitter and receiver, with connected RF or inductive antenna 195 that is employed to receive such programming commands from the physician's data processing device 200, see FIG. 1. The controller 130 then retrieves the received time intervals from the transceiver 190 and stores them in the memory 170.

The IMD 100 may additionally, or alternatively, itself determine optimal time intervals by testing various candidate time intervals and selecting the candidate time interval that leads to most optimal hemodynamic performance as assessed by monitoring a hemodynamic representing parameter. Various such hemodynamic representing parameters have been proposed in the art for traditional CRT optimization. These hemodynamic representing parameters can also be used according to the embodiments when determining optimal endocardial-to-epicardial time intervals and epicardial-to-endocardial time intervals. Non-limiting examples of such hemodynamic representing parameters include LV dP/dt, RV dP/dt, left ventricular outflow tract (LVOT) velocity time integral (VTI), fractional shortening, stroke volume, contractility, such as determined from pressure-volume loops, heart sound intensity and mitral valve regurgitation minimization.

Furthermore, an intrinsic delay between the endocardial and epicardial layer can be measured during an intrinsic beat. Since the geometrical distances between the endocardial electrode and the epicardial electrode of the epicardial LV lead are known it can be concluded whether a zone of necrotic myocytes is slowing down the endocardial-to-epicardial depolarization, see FIG. 5. The crossfiber conduction speed should be about 20 cm/s in a healthy myocardium. In addition to the measured endocardial-to-epicardial intrinsic delay a measurement of a paced endocardial event to a sensed epicardial event may also be measured. This will provide information on if the tissue located directly between the endocardial and the epicardial electrode has an impaired conduction capacity.

If it is deemed needed to synchronize the endocardial and epicardial layer a paced endocardial-to-epicardial time interval can be set. Also an intrinsic endocardial-to-epicardial time interval can be set as discussed in the foregoing. For instance, in the case of left bundle branch block (LBBB) the endocardial electrode of the epicardial LV lead will stimulate and if there is a prolonged intrinsic endocardial-to-epicardial depolarization propagation time there will also be stimulation in the epicardial layer by an epicardial electrode of the epicardial LV lead after the paced endocardial-to-epicardial time interval.

Figure 5:
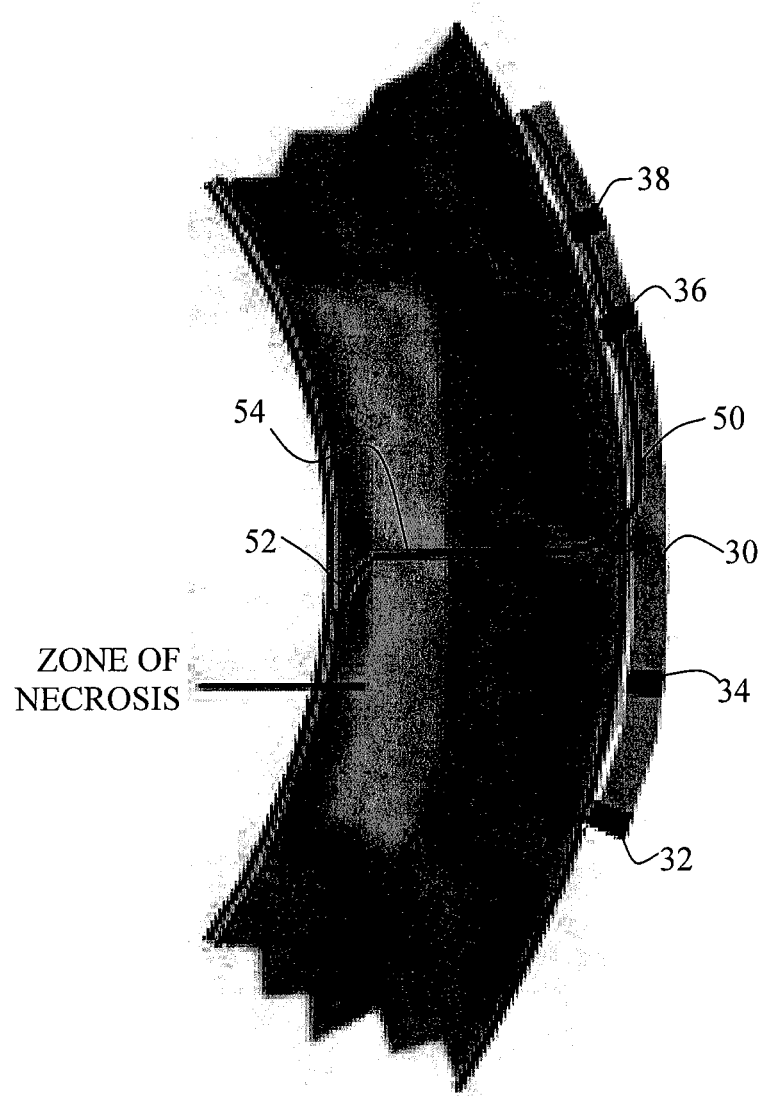
FIG. 5 is an illustration of a portion of the myocardium of a heart with an epicardial left ventricular lead according to an embodiment with the coronary vein, in which the epicardial left ventricular lead is present, is omitted to simplify the figure.

Furthermore, in the case where the intrinsic conduction to the left ventricle is normal but a subendocardial ischemia has prolonged the intrinsic endocardial-to-epicardial depolarization, see FIG. 5, the intrinsic depolarization will be sensed endocardially at an endocardial electrode 52 of the myocardium penetrating catheter 50 in the epicardial LV lead 30 and after the programmed intrinsic endocardial-to-epicardial time interval there will be an epicardial stimulation at an epicardial electrode 32, 34, 36 of the epicardial LV lead 30.

If a subendocardial ischemia has occurred causing only the epicardial electrode 32, 34, 36 to sense the depolarization, while no activity has previously been sensed endocardially, the IMD preferably uses a very short intrinsic epicardial-to-endocardial time interval to more or less immediately stimulate the endocardium using an endocardial electrode 52 of the epicardial LV lead 30.

Traditional CRT sometimes also uses atrial pacing and coordinates the atrial and ventricular pacing. The lead connector 110 then preferably comprises at least one connector terminal 111 configured to be electrically connected to an electrode of an atrial lead. The IMD 100 comprises an atrial pulse generator 145 that is configured to generate pacing pulses to be applied at the at least one atrial electrode and an atrial sensing circuit or detector 155 configured to sense electrical activity in the atrium using the at least one atrial electrode.

Atrial and ventricular pacing can then be coordinated by the controller 130 by having access to a paced and/or intrinsic atrioventricular (AV) time interval, see reference numbers 131, 133 in FIG. 6. Thus, spontaneous depolarization at the atrium as sensed by the atrial sensing circuit 155 starts an intrinsic AV time interval in the controller 130. If no depolarization is sensed at an endocardial electrode of the epicardial LV lead, at an epicardial electrode of the epicardial LV lead or at an electrode of the RV lead, depending on which of the previously described embodiments that is employed by the IMD 100, the controller 130 controls the ventricular pulse generator 140 to generate a pacing pulse to be applied to the endocardial electrode, the epicardial electrode or the RV electrode. Correspondingly, application of an atrial pacing pulse by the atrial pulse generator 145 at an atrial electrode starts a paced AV time interval.

In these embodiments, the IMD 100 can therefore use intrinsic/paced AV time intervals and/or intrinsic/paced VV time intervals in addition to the intrinsic/paced endocardial-to-epicardial (and/or epicardial-to-endocardial) time interval.

It is understood that in order to provide stimulation therapy in different heart chambers, the ventricular and atrial pulse generators 140, 145 may include dedicated, independent pulse generators, multiplexed pulse generators, or shared pulse generators. The pulse generators 140, 145 are controlled by the controller 130 via appropriate control signals, respectively, to trigger or inhibit the stimulating pulses.

Accordingly, the ventricular and atrial sensing circuits 150, 155 may include dedicated sense amplifiers, multiplexed amplifiers, or shared amplifiers. The switch 120 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 150, 155 preferably employs one or more low power, precision amplifiers with programmable gain and/or automatic gain control, band-pass filtering, and a threshold detection circuit, as known in the art, to selectively sense the cardiac signal of interest.

The outputs of the ventricular and atrial sensing circuits 150, 155 are connected to the controller 130, which, in turn, is able to trigger or inhibit the ventricular and atrial pulse generators 140, 145, respectively, in a demand fashion in response to the absence or presence of cardiac activity in the appropriate chambers of the heart.

The controller 130 of the IMD 100 is preferably in the form of a programmable microcontroller 130 that controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 130 is configured to process or monitor input signals as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

Furthermore, the controller 130 is also typically capable of analyzing information output from the sensing circuits 150, 155 to determine or detect whether and to what degree tissue capture has occurred and to program a pulse, or pulse sequence, in response to such determinations. The sensing circuits 150, 155, in turn, receive control signals over signal lines from the controller 130 for purposes of controlling the gain, threshold, polarization charge removal circuitry, and the timing of any blocking circuitry coupled to the inputs of the sensing circuits 150, 155 as is known in the art.

The optional electronic configuration switch 120 includes a plurality of switches for connecting the desired connector terminals 111-119 to the appropriate I/O circuits, thereby providing complete electrode programmability. Accordingly, the electronic configuration switch 120, in response to a control signal from the controller 130, determines the polarity of the stimulating pulses (e.g. unipolar, bipolar, combipolar, etc.) by selectively closing the appropriate combination of switches (not shown) as is known in the art.

Cardiac signals are applied to inputs of an intracardiac electrogram (IEGM) processor 160 connected to the lead connector 110. The IEGM processor 160 is preferably in the form of an analog-to-digital (ND) data acquisition unit configured to acquire IEGM signals, convert the raw analog data into a digital signal, and store the digital signals for later processing and/or transmission to the data processing device by the transceiver 190. The IEGM processor 160 is coupled to the atrial lead, the right ventricular lead and/or the epicardial LV lead and optionally a case electrode through the switch 120 to sample cardiac signals across any pair of desired electrodes.

While a particular multi-chamber device is shown in FIG. 6, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination.

The IMD 100 comprises a housing, often denoted as can or case in the art. The housing can act as return electrode (case electrode) for unipolar leads, which is well known in the art.

The IMD 100 additionally includes a battery 180 that provides operating power to all of the circuits shown in FIG. 6.

Figure 7:
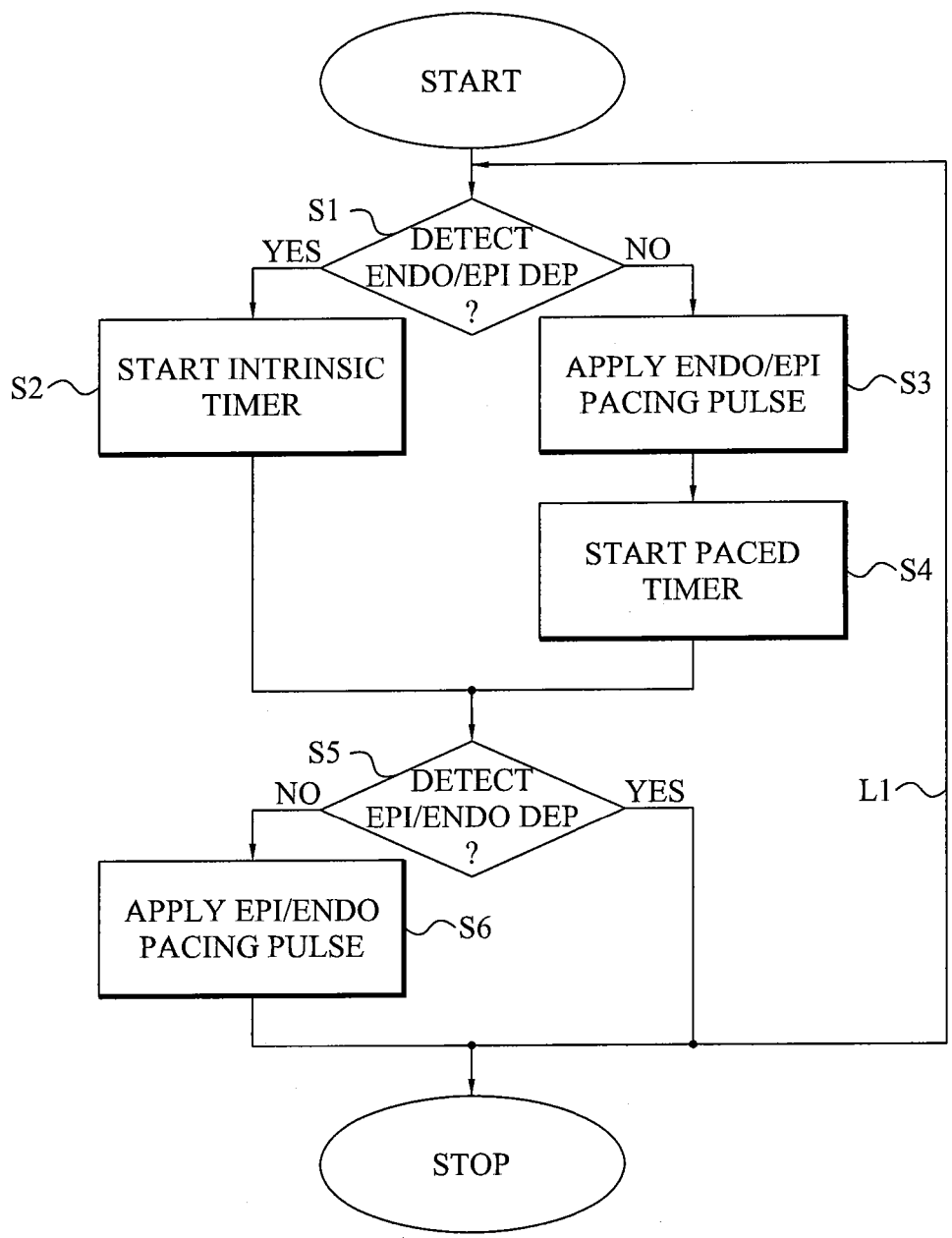
FIG. 7 is flow diagram illustrating embodiments of a cardiac resynchronization therapy method.

FIG. 7 is a flow diagram illustrating various embodiments of a cardiac resynchronization therapy method. The method starts in step S1, which monitors for an endocardial (or epicardial) depolarization at an endocardial (or epicardial) electrode of the epicardial LV lead. If such a spontaneous depolarization is detected in step S1 an intrinsic timer representing an intrinsic endocardial-to-epicardial (or epicardial-to-endocardial) time interval is started. During the intrinsic time interval as defined by the intrinsic timer the method monitors for epicardial (or endocardial) depolarization on an epicardial (or endocardial) electrode of the epicardial LV lead in step S5. If such an epicardial (or endocardial) depolarization is detected for a cardiac cycle prior to expiry of the intrinsic time interval, the method ends for the current cardiac cycle and returns back to step S1 for the next cardiac cycle. However, if no epicardial (or endocardial) depolarization is detected in step S5 after expiry of the intrinsic time interval, the method continues to step S6 where an epicardial (or endocardial) pacing pulse is applied at the epicardial (or endocardial) electrode. The method then continues to step S1 for the next cardiac cycle, which is schematically illustrated by the line L1.

If no endocardial (or epicardial) depolarization is detected for the cardiac cycle in step S1 the method instead continues to step S3. Step S3 applies an endocardial (or epicardial) pacing pulse to the endocardial (or epicardial) electrode of the epicardial LV lead. This triggers the start of a paced timer in step S4, which represents a paced endocardial-to-epicardial (or epicardial-to-endocardial) time interval. The method then continues to step S5, which, during the paced time interval, monitors for any epicardial (or endocardial) depolarization at the epicardial (or endocardial) electrode. The method then continues to step S1 for a next cardiac cycle or to step S6 depending on whether such an epicardial (or endocardial) depolarization is detected in step S5 prior to expiry of the paced time interval.

The loop formed by the steps S1-S6 is then repeated for a next cardiac cycle. Note that for some cardiac cycles the method could proceed through steps S1, S2, S5 or S1, S2, S5, S6, whereas for other cardiac cycles the method instead proceeds through steps S1, S3, S4, S5 or S1, S3, S4, S5, S6.

FIG. 8 is a flow diagram illustrating an additional step of the CRT method according to an embodiment. The method then starts in step S10, which applies a pacing pulse at a basal epicardial electrode of the epicardial LV lead to thereby achieve basal ventricular depolarization prior to any intrinsic or paced endocardial (or epicardial) depolarization of the left ventricle. The method then continues from step S10 to step S1 of FIG. 7.

Figure 9:
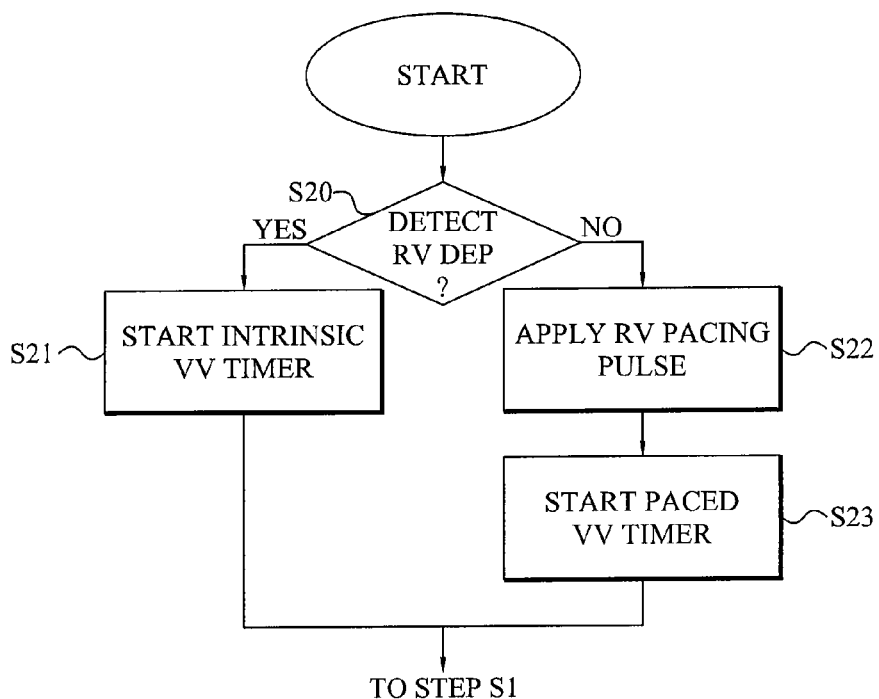
FIG. 9 is a flow diagram illustrating additional steps according to an embodiment of the cardiac resynchronization therapy method.

FIG. 9 is a flow diagram illustrating additional steps of the CRT method that enables both right ventricular and left ventricular pacing. The method starts in step S20 or continues from step S10 in FIG. 8. Step S20 monitors for any right ventricular depolarization. If such a spontaneous depolarization is detected in step S20, the method continues to step S21 where an intrinsic VV timer is started and represents the intrinsic VV time interval. The method then continues to step S1 in FIG. 7 which monitors for any endocardial (or epicardial) depolarization during the intrinsic VV time interval and will apply an endocardial (or epicardial) pacing pulse following the end of the intrinsic VV time interval if no endocardial (or epicardial) depolarization is detected prior to expiry of the intrinsic VV time interval.

If no RV depolarization is detected in step S20, such as following expiry of an AV time interval or a defined RR time interval corresponding to a defined length of a cardiac cycle, the method continues to step S22. Step S22 applies an RV pacing pulse at an electrode of the right ventricular lead. A next step S23 starts a paced VV timer that represents the paced VV time interval. The method then continues to step S1 in FIG. 7 which monitors for any endocardial (or epicardial) depolarization during the paced W time interval and will apply an endocardial (or epicardial) pacing pulse following the end of the intrinsic VV time interval if no endocardial (or epicardial) depolarization is detected prior to expiry of the paced VV time interval.

Figure 10:
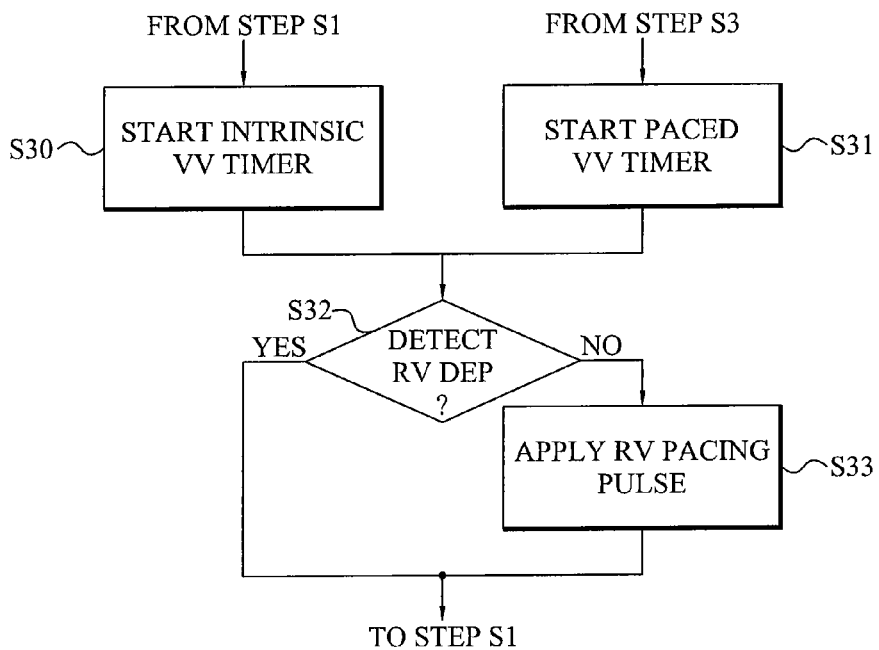
FIG. 10 is a flow diagram illustrating additional steps according to an embodiment of the cardiac resynchronization therapy method.

FIG. 10 is a flow diagram illustrating additional steps of the CRT method according to various embodiments. In an embodiment, the method continues from step S1 in FIG. 7 where spontaneous endocardial (or epicardial) depolarization is detected. This depolarization detection not only starts the intrinsic timer in step S2 but also starts the intrinsic VV timer in step S30 representing the intrinsic VV time interval. The method then continues to step S32, which is conducted at least partly in parallel with step S5 of FIG. 7 according to an embodiment. Step S32 monitors for any RV depolarization. If such an RV depolarization is detected in step S32 prior to expiry of the intrinsic VV time interval the method continues to step S1 of FIG. 7 for the next cardiac cycle. However, if no RV depolarization is detected in step S32 when the intrinsic VV time interval expires, the method continues from step S32 to step S33. Step S33 applies an RV pacing pulse to an electrode of the RV lead. The method then continues to step S1 of FIG. 7.

In another embodiment, the method continues from step S3 of FIG. 7 where an endocardial (or epicardial) pacing pulse is applied to the left ventricle. A next step S31, which is performed in parallel with step S4 of FIG. 7, starts a paced VV timer representing the paced VV time interval. The method then continues to step S32 which monitors for any RV depolarization during the paced VV time interval. The method then continues back to step S1 if such an RV depolarization is detected in step S32 prior to expiry of the paced VV time interval or to step S33 if no such RV depolarization is detected. Step S33 then applies an RV pacing pulse as previously described herein.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable medical device comprising:
a lead connector connectable to an epicardial left ventricular lead comprising:
at least one epicardial electrode provided in connection with a distal end of the epicardial left ventricular lead and electrically connected to a respective electrode terminal provided in connection with an opposite, proximal end of the epicardial left ventricular lead; and
a lumen housing a myocardium penetrating catheter with at least one endocardial electrode electrically connected to a respective electrode terminal provided in connection with the opposite, proximal end of the epicardial left ventricular lead;
wherein the lead connector comprises multiple connector terminals, each of which is electrically connectable to a respective electrode terminal of the epicardial left ventricular lead;
a ventricular pulse generator connected to the lead connector and configured to generate pacing pulses to be applied to the at least one epicardial electrode and to the at least one endocardial electrode; and
a pulse generator controller connected to the ventricular pulse generator and configured to control the ventricular pulse generator to i) apply a pacing pulse to one of the at least one epicardial electrode and the at least one endocardial electrode following expiry of an intrinsic time interval from detection of a depolarization at the other of the at least one epicardial electrode and the at least one endocardial electrode if no depolarization is detected at the at least one epicardial electrode and the at least one endocardial electrode following detection of the depolarization but prior to expiry of the intrinsic time interval for a cardiac cycle, and/or ii) apply a pacing pulse to the one of the at least one epicardial electrode and the at least one endocardial electrode following expiry of a paced time interval from application of a pacing pulse at the other of the at least one epicardial electrode and the at least one endocardial electrode if no depolarization is detected at the at least one epicardial electrode and the at least one endocardial electrode following application of the pacing pulse at the other of the at least one epicardial electrode and the at least one endocardial electrode but prior to expiry of the paced time interval for a cardiac cycle.

2. The implantable medical device according to claim 1, wherein the pulse generator controller is configured to control the ventricular pulse generator to i) apply a pacing pulse to the at least one epicardial electrode following expiry of an intrinsic endocardial-to-epicardial time interval from detection of an endocardial depolarization at the at least one endocardial electrode if no epicardial depolarization is detected at the at least one epicardial electrode following detection of the endocardial depolarization but prior to expiry of the intrinsic endocardial-to-epicardial time interval for a cardiac cycle, and/or ii) apply a pacing pulse to the at least one epicardial electrode following expiry of a paced endocardial-to-epicardial time interval from application of a pacing pulse at the at least one endocardial electrode if no epicardial depolarization is detected at the at least one epicardial electrode following application of the pacing pulse at the at least one endocardial electrode but prior to expiry of the paced endocardial-to-epicardial time interval for a cardiac cycle.

3. The implantable medical lead according to claim 1, wherein
the epicardial left ventricular lead further comprises a basal epicardial electrode provided on the epicardial left ventricular lead to be positioned at or adjacent to a basal portion of a left ventricle of a heart, the basal epicardial electrode is electrically connected to an electrode terminal provided in connection with the opposite, proximal end of the epicardial left ventricular lead;
wherein the ventricular pulse generator is configured to generate pacing pulses to be applied at the basal epicardial electrode; and
wherein the pulse generator controller is configured to control the ventricular pulse generator to apply a pacing pulse at the basal epicardial electrode prior to detection of the depolarization for the cardiac cycle or prior to application of the pacing pulse at the other of the at least one epicardial electrode and the at least one endocardial electrode for the cardiac cycle.

4. The implantable medical lead according to claim 1, wherein
the lead connector is connectable to a right ventricular lead comprising at least one electrode provided in connection with a distal end of the right ventricular lead and electrically connected to a respective electrode terminal provided in connection with an opposite, proximal end of the right ventricular lead,
the lead connector comprises at least one further connector terminal, each of which is electrically connectable to a respective electrode terminal of the right ventricular lead;
the ventricular pulse generator is configured to generate pacing pulses to be applied at the at least one electrode of the right ventricular lead; and
the pulse generator controller is configured to control the ventricular pulse generator to apply a pacing pulse at the other of the at least one epicardial electrode and the at least one endocardial electrode i) following expiry of an intrinsic ventricular-to-ventricular time interval from detection of a depolarization at an electrode of the right ventricular lead if no depolarization is detected at the other of the at least one epicardial electrode and the at least one endocardial electrode following detection of the depolarization at the electrode of the right ventricular lead but prior to expiry of the intrinsic ventricular-to-ventricular time interval for the cardiac cycle, or ii) following expiry of a paced ventricular-to-ventricular time interval from application of a pacing pulse at an electrode of the right ventricular lead if no depolarization is detected at the other of the at least one epicardial electrode and the at least one endocardial electrode following application of the pacing pulse at the electrode of the right ventricular lead but prior to expiry of the paced ventricular-to-ventricular time interval for the cardiac cycle.

5. The implantable medical lead according to claim 1, wherein
the lead connector is connectable to a right ventricular lead comprising at least one electrode provided in connection with a distal end of the right ventricular lead and electrically connected to a respective electrode terminal provided in connection with an opposite, proximal end of the right ventricular lead,
the lead connector comprises at least one further connector terminal, each of which is electrically connectable to a respective electrode terminal of the right ventricular lead;
the ventricular pulse generator is configured to generate pacing pulses to be applied at the at least one electrode of the right ventricular lead; and
the pulse generator controller is configured to control the ventricular pulse generator to apply a pacing pulse at the at least one electrode of the right ventricular lead i) following expiry of an intrinsic ventricular-to-ventricular time interval from detection of a depolarization at the other of the at least one epicardial electrode and the at least one endocardial electrode if no depolarization is detected at the electrode of the right ventricular lead following detection of the depolarization at the other of the at least one epicardial electrode and the at least one endocardial electrode but prior to expiry of the intrinsic ventricular-to-ventricular time interval for the cardiac cycle, or ii) following expiry of a paced ventricular-to-ventricular time interval from application of a pacing pulse at the other of the at least one epicardial electrode and of the at least one endocardial electrode if no depolarization is detected at an electrode of the right ventricular lead following application of the pacing pulse at the other of the at least one epicardial electrode and the at least one endocardial electrode for the cardiac cycle.

6. A cardiac resynchronization therapy method comprising:
detecting a depolarization from at least one epicardial electrode provided in connection with a distal end of an epicardial left ventricular lead and from at least one endocardial electrode arranged on a myocardium penetrating catheter at least partly present in a lumen of the epicardial left ventricular lead;
monitoring for a depolarization at the other of the at least one epicardial electrode and the at least one endocardial electrode; and
applying a pacing pulse at the other of the at least one epicardial electrode and the at least one endocardial electrode following expiry of an intrinsic time interval from detection of the depolarization at the one of the at least one epicardial electrode and the at least one endocardial electrode if no depolarization is detected at the other of the at least one epicardial electrode and the at least one endocardial electrode following detection of the depolarization at the at least one epicardial electrode and the at least one endocardial electrode but prior to expiry of the intrinsic time interval for a cardiac cycle.

7. The method according to claim 6, wherein
detecting the depolarization comprises detecting an endocardial depolarization at least one endocardial electrode;
monitoring for the depolarization comprises monitoring for an epicardial depolarization from the at least one epicardial electrode; and
applying the pacing pulse comprises applying a pacing pulse at the at least one epicardial electrode following expiry of an intrinsic endocardial-to-epicardial time interval from detection of the endocardial depolarization if no epicardial depolarization is detected following detection of the endocardial depolarization but prior to expiry of the intrinsic endocardial-to-epicardial time interval for a cardiac cycle.

8. The method according to claim 6, further comprising applying a pacing pulse at a basal epicardial electrode, provided on the epicardial left ventricular lead and positioned at or adjacent to a basal portion of a left ventricle of a heart, prior to detection of the depolarization at the one of the at least one epicardial electrode and the at least one endocardial electrode for the cardiac cycle.

9. A cardiac resynchronization therapy method comprising:
- applying a pacing pulse at one of at least one epicardial electrode provided in connection with a distal end of an epicardial left ventricular lead and at least one endocardial electrode arranged on a myocardium penetrating catheter at least partly present in a lumen of the epicardial left ventricular lead;
- monitoring for a depolarization at the other of the at least one epicardial electrode and the at least one endocardial electrode; and
- applying a pacing pulse at the other of the at least one epicardial electrode and the at least one endocardial electrode following expiry of a paced time interval from application of the pacing pulse at the one of the at least one epicardial electrode and the at least one endocardial electrode if no depolarization is detected at the other of the at least one epicardial electrode and the at least one endocardial electrode following application of the pacing pulse at the at least one epicardial electrode and the at least one endocardial electrode but prior to expiry of the paced time interval for a cardiac cycle.

10. The method according to claim 9, wherein
- applying the pacing pulse comprises applying a pacing pulse at an endocardial electrode of the at least one endocardial electrode;
- monitoring for the depolarization comprises monitoring for an epicardial depolarization at the at least one epicardial electrode; and
- applying the pacing pulse comprises applying a pacing pulse to the at least one epicardial electrode following expiry of a paced endocardial-to-epicardial time interval from application of the pacing pulse at the endocardial electrode if no epicardial depolarization is detected following application of the pacing pulse at the endocardial electrode but prior to expiry of the paced endocardial-to-epicardial time interval for a cardiac cycle.

11. The method according to claim 9, further comprising applying a pacing pulse at a basal epicardial electrode, provided on the epicardial left ventricular lead and positioned at or adjacent to a basal portion of a left ventricle of a heart, prior to application of the pacing pulse at the at least one epicardial electrode and the at least one endocardial electrode for the cardiac cycle.

12. The method according to claim 6, further comprising applying a pacing pulse at the one of the at least one epicardial electrode and the at least one endocardial electrode following expiry of an intrinsic ventricular-to-ventricular time interval from detection of a depolarization at an electrode of at least one electrode of a right ventricular lead if no depolarization is detected at the least one epicardial electrode and the at least one endocardial following detection of the depolarization at the electrode of the right ventricular lead but prior to expiry of the intrinsic ventricular-to-ventricular time interval for the cardiac cycle.

13. The method according to claim 6, further comprising applying a pacing pulse at an electrode of at least one electrode of a right ventricular lead following expiry of an intrinsic ventricular-to-ventricular time interval from detection of a depolarization at the at least one epicardial electrode and the at least one endocardial electrode if no depolarization is detected at the electrode of the right ventricular lead following detection of the depolarization at the one of the at least one epicardial electrode and the at least one endocardial electrode but prior to expiry of the intrinsic ventricular-to-ventricular time interval for the cardiac cycle.

14. The method according to claim 6, further comprising applying a pacing pulse at the at least one epicardial electrode and the at least one endocardial electrode following expiry of a paced ventricular-to-ventricular time interval from application of a pacing pulse at an electrode of at least one electrode of a right ventricular lead if no depolarization is detected at the the at least one epicardial electrode and the at least one endocardial electrode following expiry of a paced ventricular-to-ventricular time interval from application of the pacing pulse at the electrode of the right ventricular lead but prior to expiry of the paced ventricular-to-ventricular time interval for the cardiac cycle.

15. The method according to claim 6, further comprising applying a pacing pulse at an electrode of at least one electrode of a right ventricular lead following expiry of a paced ventricular-to-ventricular time interval from application of a pacing pulse at the one of the at least one epicardial electrode and the at least one endocardial electrode if no depolarization is detected at the electrode of the right ventricular lead following expiry of a paced ventricular-to-ventricular time interval from application of the pacing pulse at the at least one epicardial electrode and the at least one endocardial electrode but prior to expiry of the paced ventricular-to-ventricular time interval for the cardiac cycle.

* * * * *